United States Patent
Kopreski

(10) Patent No.: US 8,163,524 B2
(45) Date of Patent: *Apr. 24, 2012

(54) COMPARATIVE ANALYSIS OF EXTRACELLULAR RNA SPECIES

(75) Inventor: Michael S. Kopreski, Long Valley, NJ (US)

(73) Assignee: OncoMedx, Inc., Long Valley, NJ (US)

(*) Notice: Subject to any disclaimer, the term of this patent is extended or adjusted under 35 U.S.C. 154(b) by 642 days.

This patent is subject to a terminal disclaimer.

(21) Appl. No.: 11/857,414

(22) Filed: Sep. 18, 2007

(65) Prior Publication Data

US 2009/0111097 A1 Apr. 30, 2009

Related U.S. Application Data

(63) Continuation-in-part of application No. 11/346,590, filed on Feb. 2, 2006, now Pat. No. 7,785,842, which is a continuation-in-part of application No. 10/658,873, filed on Sep. 5, 2003, now abandoned, which is a continuation-in-part of application No. 10/013,868, filed on Oct. 30, 2001, now Pat. No. 6,939,671, which is a continuation of application No. 09/155,152, filed on Sep. 22, 1998, now Pat. No. 6,329,179.

(51) Int. Cl.
C12P 19/34 (2006.01)
C12Q 1/68 (2006.01)
C07H 21/02 (2006.01)
C07H 21/04 (2006.01)
C07H 21/00 (2006.01)

(52) U.S. Cl. ...... 435/91.2; 435/6.1; 435/6.12; 435/91.1; 536/23.1; 536/24.3; 536/24.33; 536/25.3

(58) Field of Classification Search ............ 435/6, 91.1, 435/91.2, 183, 6.12, 6.1; 436/94; 536/23.1, 536/24.3, 24.33, 25.3
See application file for complete search history.

(56) References Cited

U.S. PATENT DOCUMENTS

| | | |
|---|---|---|
| 4,350,156 A | 9/1982 | Malchesky |
| 4,631,130 A | 12/1986 | Watanabe |
| 4,683,195 A | 7/1987 | Mullis et al. |
| 4,699,877 A | 10/1987 | Cline et al. |
| 4,738,927 A | 4/1988 | Taniguchi |
| 4,874,853 A | 10/1989 | Rossi |
| 4,874,858 A | 10/1989 | Magistro |
| 4,999,290 A | 3/1991 | Lee |
| 5,087,617 A | 2/1992 | Smith |
| 5,098,890 A | 3/1992 | Gerwitz et al. |
| 5,124,246 A | 6/1992 | Urdea et al. |
| 5,155,018 A | 10/1992 | Gillespie et al. |
| 5,217,889 A | 6/1993 | Roninson et al. |
| 5,274,087 A | 12/1993 | Barnett et al. |
| 5,300,635 A | 4/1994 | MacFarlane |
| 5,409,818 A | 4/1995 | Davey et al. |
| 5,429,923 A | 7/1995 | Seidman |
| 5,470,724 A | 11/1995 | Ahern |
| 5,506,106 A | 4/1996 | Croce |
| 5,532,220 A | 7/1996 | Lee |
| 5,576,178 A | 11/1996 | Emanuel et al. |
| 6,001,987 A | 12/1999 | Perron |
| 6,051,374 A | 4/2000 | Simons |
| 6,057,105 A | 5/2000 | Hoon |
| 6,329,179 B1 | 12/2001 | Kopreski |
| 6,344,317 B2 | 2/2002 | Urnovitz |
| 6,607,898 B1 | 8/2003 | Kopreski |
| 6,759,217 B2 | 7/2004 | Kopreski |
| 6,794,135 B1 | 9/2004 | Kopreski |
| 6,916,634 B2 | 7/2005 | Kopreski |
| 6,939,671 B2 | 9/2005 | Kopreski |
| 2004/0058331 A1 | 3/2004 | Akagi |

FOREIGN PATENT DOCUMENTS

| | | |
|---|---|---|
| DE | 3717212 | 12/1988 |
| WO | 90/09456 A1 | 8/1990 |
| WO | 97/35589 A | 10/1997 |
| WO | 98/14617 A | 4/1998 |
| WO | 99/67397 | 12/1999 |

OTHER PUBLICATIONS

Ma et al., Plasma RNA as an alternative to cells for monitoring molecular response in patients with chronic myeloid leukemia. Haematologica/the hematology Journal 92, 170-175, 2007.*
Schüler et al., Chromosomal translocation t(14;18) in healthy individuals. Seminars in Caner Biology, 13, 203-209, 2003.*
The definition of "BCR-ABL fusion gene". Printed on Jun. 18, 2010 from ncbi.nlm.nih.gov.*
Brassesco, Leukemia/lymphoma-associated gene fusion in normal individuals. Genetics and Molecular Research, 7, 782-790, 2008.*
Office Action, Non-Final Rejection mailed on Nov. 4, 1999 for U.S. Appl. No. 09/155,152.
Office Action, Non-Final Rejection mailed on Apr. 20, 2000 for U.S. Appl. No. 09/155,152.
Office Action, Final Rejection mailed on Oct. 25, 2000 for U.S. Appl. No. 09/155,152.
Office Action, Final Rejection mailed on Apr. 20, 2001 for U.S. Appl. No. 09/155,152.
Office Action, Non-Final Rejection mailed on Nov. 4, 1999 for U.S. Appl. No. 09/210,671.
Office Action, Non-Final Rejection mailed on Aug. 7, 2002 for U.S. Appl. No. 09/966,515.
Office Action, Non-Final Rejection mailed on Nov. 19, 2002 for U.S. Appl. No. 09/966,515.
Office Action, Non-Final Rejection mailed on Dec. 4, 2002 for U.S. Appl. No. 10/013,868.
Office Action, Final Rejection mailed on May 20, 2003 for U.S. Appl. No. 10/013,868.
Office Action, Non-Final Rejection mailed on Oct. 25, 2002 for U.S. Appl. No. 10/013,294.
Office Action, Non-Final Rejection mailed on Aug. 30, 2005 for U.S. Appl. No. 10/201,382.
Office Action, Final Rejection mailed on Mar. 15, 2006 for U.S. Appl. No. 10/201,382.

(Continued)

Primary Examiner — Frank W Lu
(74) Attorney, Agent, or Firm — McDonnell Boehnen Hulbert & Berghoff

(57) ABSTRACT

The invention provides methods for detecting tumor-associated RNA in plasma, serum, and other bodily fluids. In particular, the invention provides methods for detecting translocated gene RNA, including fusion gene RNA, in plasma or serum or other bodily fluids.

8 Claims, No Drawings

OTHER PUBLICATIONS

Office Action, Non-Final Rejection mailed on Jan. 10, 2007 for U.S. Appl. No. 10/201,382.
Office Action, Final Rejection mailed on Sep. 10, 2007 for U.S. Appl. No. 10/201,382.
Office Action, Non-Final Rejection mailed on Nov. 16, 2005 for U.S. Appl. No. 10/288,935.
Office Action, Final Rejection mailed on Jun. 12, 2006 for U.S. Appl. No. 10/288,935.
Office Action, Non-Final Rejection mailed on Feb. 23, 2007 for U.S. Appl. No. 10/288,935.
Office Action, Final Rejection mailed on Oct. 4, 2007 for U.S. Appl. No. 10/288,935.
Office Action, Non-Final Rejection mailed on Aug. 24, 2006 for U.S. Appl. No. 10/658,873.
Office Action, Final Rejection mailed on Apr. 9, 2007 for U.S. Appl. No. 10/658,873.
Office Action, Non-Final Rejection mailed on Jan. 28, 2008 for U.S. Appl. No. 10/658,873.
Office Action, Final Rejection mailed on Jul. 10, 2008 for U.S. Appl. No. 10/658,873.
Office Action, Non-Final Rejection mailed on Dec. 15, 2006 for U.S. Appl. No. 10/684,633.
Office Action, Final Rejection mailed on Jun. 21, 2007 for U.S. Appl. No. 10/684,633.
Office Action, Non-Final Rejection mailed on Jan. 28, 2008 for U.S. Appl. No. 10/684,633.
Office Action, Non-Final Rejection mailed on May 3, 2007 for U.S. Appl. No. 10/912,367.
Office Action, Final Rejection mailed on Aug. 10, 2007 for U.S. Appl. No. 10/912,367.
Office Action, Non-Final Rejection mailed on Feb. 6, 2008 for U.S. Appl. No. 10/912,367.
Office Action, Final Rejection mailed on Dec. 1, 2008 for U.S. Appl. No. 10/912,367.
Office Action, Non-Final Rejection mailed on Apr. 2, 2008 for U.S. Appl. No. 11/216,858.
Office Action, Final Rejection mailed on Nov. 14, 2008 for U.S. Appl. No. 11/216,858.
Office Action, Non-Final Rejection mailed on Oct. 2, 2008 for U.S. Appl. No. 11/346,590.
Office Action, Non-Final Rejection mailed on Nov. 13, 2008 for U.S. Appl. No. 11/357,399.
Office Action, Non-Final Rejection mailed on Sep. 22, 2008 for U.S. Appl. No. 11/364,842.
Office Action, Non-Final Rejection mailed on Sep. 10, 2008 for U.S. Appl. No. 11/421,260.
Office Action, Non-Final Rejection mailed on Jan. 8, 2009 for U.S. Appl. No. 11/416,470.
Office Action, Non-Final Rejection mailed on Oct. 8, 2008 for U.S. Appl. No. 11/416,788.
Landgraf et al. (1991), Analytical Biochmistry 198: 86-91.
Landgraf et al. (1991), Analytical Biochemistry 193: 231-235.
Larson et al. (1991), "Radioisotope Conjugates," In: Biologic Therapy of Cancer (Ed. DeVita et al.) Lippincott: Philadelphia, pp. 496-511.
Leitzel et al. (1998), Clin. Cancer Res. 4: 3037-3043.
Leon et al. (1981), Eur. J. Cancer 17: 533-538.
Maruyama et al. (1994), Leukemia 8:40-45.
Masella et al. (1989), FEBS Lett. 246: 25-29.
McCabe et al. (1995), Cancer Research 55: 1741-1747.
Messner et al. (2000), Am. J. Clin. Pathol. 114(4): 544-549.
Miller et al. (1993), Blood 82: 1689-1694.
Patard et al. (1995), Int. J. Cancer 64: 60-64.
Penno et al. (1994), Cancer Research 54: 1381-1387.
Peoples et al. (1995), Proc. Natl. Acad. Sci. U. S. A. 92: 432-436.
Pfleiderer et al. (1995), Int. J. Cancer. 64: 135-139.
Polushin et al. (1994), Nucleic Acids Research 22: 5492-5496.
Rashtchian (1994), PCR Methods Applic. 4: S83-S91.
Reddi and Holland (1976), Proc. Natl. Acad. Sci. U. S. A. 73: 2308-2310.
Ricchiuti et al. (1997), Clin. Chem. 43(6): 990-995.
Ricchiuti et al. (1999), Clin. Chem. 45(6): A144-A145.
Ricchiuti et al. (1999), Clin. Chem. 45(12): 2129-2135.
Rieber and Bacalao (1974), Proc. Natl. Acad. Sci. U. S. A. 71: 4960-4964.
Roggenbuck et al. (1991), J. Virol. 65: 5068-72.
Rosenberg-Nicolson et al. (1992), J. Cell Biochem. 50: 43-52.
Rosenzweig et al. (1981), New England Journal of Medicine 325(25): 1753-1760.
Rosi et al. (1988), Cancer Lett. 39: 153-160.
Saiki et al. (1989), Science 233: 1076-1078.
Sakakura et al. (1994), Br. J. Cancer 70: 1060-1066.
Schlom (1991), "Antibodies in cancer therapy: basic principles of monaclanal antibodies," In: Biologic Therapy of Cancer, (Ed. DeVita et al.) Lippincott: Philadelphia, pp. 464-481.
Serra et al. (2001), Neurological Sciences 22(2): 171-173.
Shen et al. (1995), Proc. Natl. Acad. Sci. U. S. A. 92: 6778-6782.
Shutack et al. (1968), J. Am. Osteopath. Assoc. 67(9): 1051-1053.
Skorski et al. (1994), Proc. Natl. Acad. Sci. U. S. A. 91: 4504-4508.
Smith et al. (1991), Lancet 338: 1227-1229.
Sooknanan et al. (1993), Experimental Hematology 21: 1718-1724.
Spiegelman et al. (1969), The Harvey Lectures No. 64, pp. 1-67.
Stock et al. (1997) J. Olin. Oncology 15: 26-36.
Stroun et al. (1978), Cancer Res. 38(10): 3546-3554.
Stroun et al. (1989), Oncology 46: 318-322.
Tamamiyagi et al. (1996), J. Dermatol. Sci. 11(2): 154-60.
Taylor and Blak (1985), "Shedding of Plasma Membrane Fragments. Neoplastic and Developmental Importance," In: The Cell Surface in Development and Cancer, Develop. Biol. 3: 33-57 Ed. Steinberg. Plenum Press: New York.
Urdea et al. (1991), Nucleic Acids Research Symposium Series 24: 197-200.
Urdea et al. (1993), AIDS 7(suppl. 2): S11-S14.
Vandamme et al. (1995), J. Virological Methods 52: 121-132.
Abravaya et al. (1995), Nucleic Acids Res. 23: 675-682.
Alkema et al. (1993), Human Mol. Genet. 2: 1597-1603.
Allouche et al. (1995), Leukemia 9(1): 77-86.
Aoki et al. (1995), Cancer Res. 55: 3810-3816.
Barz et al. (1985), Biochim. Biophys. Acta 814(1): 77-84.
Bauer et al. (1995), Scand. J. Immunol. 42: 317-323.
Blackburn et al. (1991), Olin. Chem. 37(9): 1534-1539.
Bobo et al. (1990), J. Clin. Micro., 28: 1968-1973.
Bocchia et al. (1995), Blood 85: 2680-2684.
Boom et al. (1990), J. Clin. Micro. 28: 495-503.
Boom et al. (1991), J. Clin. Micro. 29: 180-181.
Brossart et al. (1994), J. Immunotherapy 15: 38-41.
Buchman et al. (1993), PCR Methods Applic. 3: 28-31.
Carr et al. (1985), Cancer Res. 45: 5944-5951.
Cheung et al. (1994), J. Clin. Micro. 32: 2593-2597.
Chirgwin et al. (1979), Biochemistry 18: 5294-5299.
Chomczynski and Mackey (1995), BioTechniques 19: 942-945.
Chomczynski and Mackey (1995), Analytical Biochemistry 225: 163-164.
Chomczynski et al. (1987), Analytical Biochemistry 162: 156-159.
Chomczynski (1993), Biotech 15: 532-537.
Chu et al. (1995), Mol. Cell Biol. 15: 179-185.
Cohen (1991), "Biochemical Therapy: Antisense Compounds," Biologic Therapy of Cancer (DeVita, et al. eds) J.B. Lippincott: Philadelphia, pp. 763-775.
Colomer et al. (1994), Br. J. Cancer 70: 819-825.
Coutlee et al. (1989), Analytical Biochemistry 181: 96-105.
Datta et al. (1994), Journal of Clinical Oncology 12: 475-482.
Davidova and Shapot (1970), FEBS Lett. 6: 349-351.
DiCesare et al. (1993), BioTechniques 15: 152-157.
Doi et al. (1996), Int. J. Cancer 65: 454-459.
Feng et al. (1995), Science 269: 1236-1241.
Garbarz et al. (1992), Blood 80(4): 1066-1073.
Gerhard et al. (1994), J. Clin. Oncol. 12: 725-729.
Ghossein et al. (1995), J. Clin. Oncol. 13: 1195-1200.
Guin et al. (1975), Biochemical Medicine 13(3): 224-230.
Higashiyama et al. (1995), Cancer Res. 55: 6040-6044.
Hoon et al. (1995), J. Clin. Oncol. 13: 2109-2116.
Hoover et al. (1991), "Immunotherapy by Active Specific Immunization: Clinical Applications," Biologic Therapy of Cancer (DeVita, et al. eds) J.B. Lippincott: Philadelphia, pp. 670-682.

Imai et al. (1992), J. Virol. Methods 36: 181-184.
Juckett and Rosenberg (1982), Cancer Research 42: 3565-3573.
Kahn et al. (1991), Oncogene 6: 1079-1083.
Kamm and Smith (1972), Clinical Chemistry 18: 519-522.
Karet et al. (1994), Analytical Biochemistry 220: 384-390.
Katz et al. (1995), Cancer 75: 1642-1648.
Kievits et al. (1991), J. Virological Methods 35: 273-286.
Kim et al. (1994), Science 266: 2011-2015.
Komeda et al. (1995), Cancer 75: 2214-2219.
Kopreski et al. (1999), Clin. Cancer Res. 5: 1961-1965.
Kopreski et al. (2000), Ann. N.Y. Acad. Sci. 906: 124-128.
Vitetta et al. (1991), "Immunatoxins," In: Biologic Therapy of Cancer, (Ed. DeVita et al.) Lippincott: Philadelphia pp. 482-495.
Wang et al. (1989), "Quantitation of mRNA by the polymerase chain reaction," Proc. Natl. Acad. Sci. U.S.A. 86: 9717-9721.
Wieczorek et al. (1987), Cancer Research 47: 6407-6412.
Wieczorek et al. (1989), Schweiz med Wschr 119: 1342-1343.
Wieczorek et al. (1985), Proc. Natl. Acad. Sci. U.S.A. 82: 3455-3459.
Wiedmann et al. (1994), PCR Methods Applic. 3: 551-564.
Yanuck et al. (1993), Cancer Research 52: 3257-3261.
Rohde et al. (2000), Clin. Cancer Res. 6: 4803-4809.
Keller et al. (1993), PCR Methods and Applications 3: 32-38.
Schmidt et al. (1995), J. Med. Virology 47: 153-160.
Agliullina et al. (1988), Eksp. Onkol (USSR) 10(4), English abstract.
Schwarz et al. (1995), Res. Virol (Paris) 146(5), 355-362.
Kato et al. (1993), Hepatology 18(1), 16-20.
Glick et al. (1994), Molecular biotechnology: Principles and applications of recombinant DNA, ASM Press: Washington DC. Table of Contents for Molecular Diagnostics (8) and Vaccines and Therapeutic Agents (9), only contents.
Persing et al (1993), Diagnostic molecular microbiology: Principles and applications, Amer. Soc. Microbiol. Washington DC, Table of Contents for Principles of Diagnostic Molecular Microbiology and Viral Pathogens, only contents.
Southall et al. (1990), Br. J. Cancer 61: 89-95.
Kopreski et al. (2001), Ann. N.Y. Acad. Sci 945: 172-178.
Yan-Sanders et al. (2002), Cancer Letters 183: 215-220.
Khimani et al. (2005), BioTechniques 38: 739-745.
Schrader et al. (2002), BMC Cancer 2: 32.
Fleischhacker et al. (2001), Ann. N.Y. Acad. Sci. 945: 179-188.
Burd et al. (1989), Proc. Natl. Acad. Sci. U.S.A. 86: 9788-9792.
Burchill et al. (1995), Br. J. Cancer 71: 278-281.
Lasheeb et al. (1997), Genitourinary Medicine 73(4): 303-305.
Mermin et al. (1991), J. Infectious Diseases 164(4): 769-772.
Kopreski et al. (2001), Clin. Chem. 47: 362, abstract 9.
Pelosi et al. (2006), Virchows Arch. 448: 7-15.
Tahara et al. (1999), Oncogene 18: 1561-1567.
Dasi et al. (2001), Lab. Investigation 81: 767-769.
Hasselmann et al. (2001), Oncol. Rep. 8: 115-118.
Chen et al. (2000), Clin. Cancer Res. 6: 3823-3826.
Silva et al. (2001), Oncol. Rep. 8: 693-696.
Miura et al. (2003), Oncology 64: 430-434.
Wong et al. (2004), J. Clin. Pathol. 57: 766-768.
Ma et al. (2007), Haematologica 92: 170-175.
Arcari et al. (1984), Nucleic Acids Res. 12: 9179-9189.
Rykova et al. (2006), Ann. N.Y. Acad. Sci. 1075: 328-333.
Hernandez et al. (1999), Leukemia 13: 2087-2093.
Zhou et al. (1998), Clin. Cancer Res. 4: 1631-1640.
Zhou et al. (2001), Breast Cancer Research and Treatment 66: 217-224.
Press et al. (1990), Oncogene 5: 953-962.
Bairey et al. (2002), Arch. Pathol. Lab. Med. 126: 574-576.
Gilmour et al. (2001), Cancer Res. 61: 2169-2716.

Reinhold et al. (2001), Clin. Chem. 47: 369, abstract 50.
Dahiya et al. (1996), Urology 48: 963-970.
LeRiche et al. (1996), J. Clin. Endocrinol. Metab. 81: 656-662.
Pfeiffer et al. (1997), Int. J. Cancer 72: 581-586.
De Luca et al. (2000), Clin. Cancer Res. 6: 1439-1444.
Schlegel et al. (1994), Int. J. Cancer 56: 72-77.
Worm et al. (1999), Hum. Pathol. 30: 222-227.
Pawlowski et al. (2000), Cancer Detect. Prey. 24: 212-223.
Walch et al. (2001), Lab. Invest. 81: 791-801.
Sarkar et al. (1993), Diagn. Mol. Pathol. 2: 210-218.
Gebhardt et al. (1998), Biochem. Biophys. Res. Comm. 247: 319-323.
Revillion et al. (1997), Clin. Chem. 43: 2114-2120.
Schneeberger et al. (1996), Anticancer Res. 16: 849-852.
Kraehn et al. (2001), Br. J. Cancer 84: 72-79.
Sagawa et al. (2001), Cancer Letters 168: 45-50.
Christoph et al. (1999). Int. J. Cancer 84: 169-173.
Latil et al. (2000), Int. J. Cancer 89: 172-176.
Zhou et al. (1996), J. Biol. Chem. 271: 10760-10766.
Kozu et al. (1995), Genomics 25: 365-371.
Gocke et al. (2001), Clin. Chem. 47: 369, abstract 51.
Poon et al. (2001), Clin. Chem. 47: 363, abstract 11.
Urnovitz et al. (1999), Clin. Diag. Lab. Immunology 6: 330-335.
Zhao et al. (1994), Circulation 90: 677-685.
Dhillon et al. (2001), Exp. Neurol. 170: 140-148.
Fleischhacker et al. (2001), Clin. Chem. 47: 369 (Oral Presentation).
Tschentscher et al. (2000), Int. J. Clin. Lab. Res. 30(1): 13-15.
Missov et al. (1999), Clinica Chimica Acta 284: 175-185.
Sarko et al. (2002), J. Emerg. Med. 23(1): 57-65.
Jurlander et al. (2000), Eur. Heart J. 21: 382-289.
Rainer et al. (2003), Clin. Chem. 50(1): 206-208.
Townsend et al. (1995), J. Mol. Cell. Cardiol. 27: 2223-2236.
Meikl et al. (1998), Leukemia 12: 311-316.
Lee et al. (1996), Proc. Natl. Acad. Sci. U.S.A. 93: 10366-10370.
Robertson et al. (1999), Nucleic Acids Res. 27(11): 2291-2298.
Fleischhacker and Schmidt (2007), Biochim. Biophys. Acta 1775: 181-232.
Lion et al. (1995), Leukemia 9: 1353-1360.
Lo et al. (1999), Clin. Chem. 45(8): 1292-1294.
Chen et al. (1999), Int. J. Cancer 83: 10-14.
Saito et al. (2001), Hepatology 33: 561-568.
Moore et al. (1990) Nucleic Acids Res. 18(7) 1921.
Moreno et al. (1992) Cancer Res. 52:5110-12.
Mori et al. (1995) Cancer Res. 55:3417-20.
Mountford et al. (1987) Lancet 1 (8537)829-34.
Nguyen (1989) BioTechniques 7:238-40.
Ozcelik et al. (1995) Clinical Cancer Research 1:907-12.
Dosaka et al. (1991) Oncogene 6:371-378.
Edmands et al. (1994) PCR Methods. Applic. 3:317-19.
Fournie et al. (1986) Analytical Biochemistry 158:250-56.
Nolte et al. (1994) J. Clin. MicroBiology 32:519-520.
Ng et al.(2002) Clin. Chem. 18:1212-17.
Silva et al. (2001) Clin. Cancer Research 7:2821-25.
Gal et al. (2001) Ann. N.Y. Acad. Sci. 945:192-94.
Durie et al. (2000) Acta. Oncol. 39:789-96.
Ng et al. (2003) Proc. Natl. Acad. Sci. USA 100:4748-53.
Rajagopal et al. (1995) Int. J. Cancer 62:661-67.
Camberi et al. (1998) Oncology 55:556-63.
El-Hefnawy et al. (2004) Clin. Chem. 50(3):564-73.
Mizuno et al. (2001) Blood 97(5):1172-79.
Eads et al. (1999) Cancer Res. 59:2302-06.
El-Deiry et al. (1991) Proc. Natl. Acad. Sci USA 88:3470-74.

* cited by examiner

COMPARATIVE ANALYSIS OF EXTRACELLULAR RNA SPECIES

This application is a continuation-in-part of U.S. Ser. No. 11/346,590, filed Feb. 2, 2006, now U.S. Pat. No. 7,785,842 which is a continuation-in-part of U.S. Ser. No. 10/658,873, filed Sep. 5, 2003, now abandoned, which is a continuation-in-part of U.S. Ser. No. 10/013,868, filed Oct. 30, 2001, now U.S. Pat. No. 6,939,671, which is a continuation of U.S. patent application, Ser. No. 09/155,152, filed Sep. 22, 1998, now U.S. Pat. No. 6,329,179 B1, which is a U.S. national phase application filed pursuant to the provisions of 35 U.S.C. §371 of International Application, Ser. No. PCT/US97/03479, filed Mar. 14, 1997, which claims the benefit of the filing date of Provisional U.S. patent application, Ser. No. 60/014,730, filed Mar. 26, 1996, the entire disclosure of each of which is hereby incorporated by reference.

BACKGROUND OF THE INVENTION

Ribonucleic acid (RNA) plays an essential role in the translation of the genetic code to produce proteins necessary for cellular function, both in normal cells and neoplastic or diseased cells. In particular, RNA including transfer RNA, messenger RNA or messenger-like RNA, and ribosomal RNA carry and translate the genetic code to sites of protein production. Further, double-stranded RNA and species therefrom, including small inhibitory RNA such as siRNA (short interfering siRNA) and micro RNA or miRNA, play an important role in silencing genetic expression. Other RNA species are found within ribonucleoproteins. For example, telomerase RNA is a critical component of telomerase, an important ribonucleoprotein highly expressed in most cancers. The pathogenesis and regulation of cancer is thus dependent upon RNA-mediated translation and/or inhibitory control of specific genetic code, said genetic code often reflecting mutational events or other alterations within deoxyribonucleic acid (DNA), including epigenetic alterations such as hypermethylation, microsatellite alterations, loss of heterozygosity, translocations including inversions and gene fusions, deletions, and point mutations. Further, other RNA species and their associated proteins, although not necessarily being directly involved in neoplastic pathogenesis or regulation, may provide recognizable characterization of neoplasia or disease by being inappropriately expressed or elevated. Such overexpression of RNA thus can delineate cancer or other disease. Recognition of the presence or overexpression of specific RNA, including both coding and non-coding RNA, can enable identification, detection, inference, monitoring, or evaluation of any neoplasm, whether benign, malignant, or premalignant, in humans and animals.

U.S. Pat. No. 6,329,179 B1, incorporated herein in its entirety, teaches that both tumor-associated and non-tumor associated RNA are detectable in plasma and serum. Total RNA is intended herein to refer to a mixture or collection of heterogeneous RNA species or fragments thereof, and is to be understood in the cancer patient to comprise both tumor-associated and non-tumor-associated RNA and further it will be understood that it can be inclusive of heterogeneous RNA of various RNA species and types, which can include messenger RNA, ribosomal RNA, transfer RNA, micro RNA, short interfering RNA, and mitochondrial RNA, and specific species thereof. RNA comprising heterogeneous RNA, such as total RNA, can be extracted from plasma or serum or other non-cellular bodily fluid fractions, the RNA of interest or its cDNA is amplified qualitatively or quantitatively, and the amplified product of an RNA or cDNA species of interest detected. Subsequent art supports these teachings by demonstrating that extracellular RNA of various RNA species are detectable in bodily fluids, for example in co-owned U.S. Pat. No. 6,607,898; Kopreski et al., 1999, *Clin. Cancer Res.* 5: 1961-1965; Dasi et al., 2001, *Lab. Investigation* 81: 767-769; Hasselmann et al., 2001, *Oncol. Rep.* 8: 115-118; Ng et al., 2002, *Clin. Chem.* 48: 1212-1217; Chen et al., 2000, *Clin. Cancer Res.* 6: 3823-3826; Silva et al., 2001, *Clin. Cancer Res.* 7: 2821-2825; Silva et al., 2001, *Oncol. Rep.* 8: 693-696; Gal et al., 2001, *Ann. NY Acad. Sci.* 945: 192-194; Durie et al., 2000, *Acta Oncol.* 39: 789-796; Fleischhacker et al., 2001, *Ann. NY Acad. Sci.* 945: 179-188; Miura et al., 2003, *Oncology* 64: 430-434; Kopreski et al., 2001, *Ann. NY Acad. Sci.* 945: 172-178; Wong et al., *J. Clin. Pathol.* 2004, 57: 766-768' and Ma et al., *Haematologica,* 2007, 92: 170-175, said references incorporated herein in their entirety. Detection of tumor-associated RNA in plasma or serum or non-cellular bodily fluid fractions thus provides a method for detecting, diagnosing, inferring, evaluating or monitoring cancer or premalignancy in a human or animal. Similarly, detection of extracellular RNA in bodily fluids enables the evaluation and monitoring of treatments and therapies for cancer and other diseases.

Neoplasia is characterized by varying degrees of invasiveness, metastatic potential, and resistance or responsiveness to particular therapies. Furthermore, these characteristics for a given neoplasia may change over time, for example by becoming progressively more malignant, invasive, metastatic, heterogeneous, undifferentiated, or treatment-resistant. Phenotypic changes often reflect underlying molecular changes. In particular, the relative ratio of particular RNA species, including coding and non-coding species, to each other, and/or to DNA, and/or to proteins can determine the characteristics of the neoplasia, and further enable the diagnosis, detection, evaluation, or monitoring of cancer and premalignancy. One group of tumor-associated RNA expressed or over-expressed in neoplastic disease are RNA associated with DNA translocations, including herein inversions and gene fusions. The presence of a specific translocation or gene fusion may further characterize a neoplastic disease.

Analysis in an absolute or relative fashion of extracellular RNA species to each other, and/or to extracellular DNA, and/or to extracellular protein, would thus be useful as a method for detecting, diagnosing, inferring, characterizing, or monitoring cancer or premalignancy in a human or animal. Said analysis further enables the selection and monitoring of treatment. Cancer treatments can target or inhibit specific gene products or gene pathways, such as for example but not limitation, fusion gene targets ore receptor tyrosine kinase targets. Cancer treatments can further target or inhibit specific mRNA targets, for example using anti-sense RNA or using siRNA therapies.

Thus, there is a need in the art for methods of comparing the amount or concentration or relative ratio of two or more plasma or serum RNA species or fragments thereof to permit diagnosis, detection, inference, evaluation, or monitoring of neoplastic disease in a human or animal. It is to be explicitly understood that said comparison of two or more RNA species may include comparison of non-mutated tumor RNA to tumor RNA; tumor RNA to non-mutated non-tumor RNA; coding RNA to coding RNA; coding RNA to non-coding RNA; and non-coding RNA to non-coding RNA; or any combination thereof. Further more a RNA may be compared to a DNA.

Furthermore, there is a need for methods of comparing the amount or concentration or ratio of one or more extracellular RNA species to the amount or concentration of total RNA or extracellular DNA or protein present in the plasma, serum, or bodily fluid of a human or animal for the diagnosing, detecting, inferring, evaluating, or monitoring cancer and other neoplastic diseases in the human or animal.

It is further understood that the present invention provides methods for detecting RNA associated with translocated DNA and gene fusions, which are often associated with neoplastic disease. Said RNA may be detected in a qualitative or quantitative fashion either itself, or in comparison to a reference RNA, or in combination with other tumor-associated RNA and/or tumor-associated DNA.

SUMMARY OF THE INVENTION

The invention provides methods for diagnosing, detecting, inferring, evaluating, or monitoring cancer and premalignancy by detecting extracellular tumor-associated RNA in plasma, serum, and other bodily fluids, the method comprising the steps of extracting RNA from the bodily fluid, amplifying a portion of the extracted RNA or cDNA therefrom for tumor-associated RNA, and detecting the amplified product or signal. In one particularly preferred aspect of this embodiment the tumor-associated RNA is RNA of a translocated gene, such as a fusion gene. In other aspects of the embodiment, the invention provides for detection of other tumor-associated RNA, including but not limited to RNA that is over-expressed in malignancy, RNA related to hormone receptors, receptor tyrosine kinase RNA, other enzymatic RNA, oncogene RNA, RNA associated with hypermethylated DNA, RNA associated with mutated DNA, inhibitory RNA including miRNA and siRNA, mitochondrial RNA, and ribonucleoprotein RNA.

The invention provides methods for diagnosing, detecting, inferring, evaluating, or monitoring cancer or other neoplastic disease such as premalignancy in a human or animal by determining the amount, concentration, ratio, or other quantitative or comparative assessment between two or more extracellular RNA species in plasma or serum or other bodily fluid from a human or animal. The invention further provides methods for comparing one or more specific extracellular RNA species in plasma or serum or bodily fluid to another within said specimen, or to extracellular total RNA, extracellular DNA, or extracellular protein within said plasma, serum, or bodily fluid specimen. The methods provided by the invention comprise qualitative or quantitative determination of the amount or concentration or ratio between at least two extracellular RNA species in a bodily fluid specimen by any of means known to the art, including but not limited to nucleic acid amplification, signal amplification, spectroscopy including mass spectroscopy, and hybridization methods using detectably-labeled probes. The methods provided by the invention further comprise qualitative or quantitative determination of a least one extracellular RNA species within a bodily fluid specimen to one or more of the following group within said specimen: total extracellular RNA, total extracellular DNA, one or more extracellular DNA species, one or more extracellular proteins. It is to be understood that within this specification, RNA species refers to RNA selected from one or more of the group comprising messenger RNA (mRNA), inhibitory (interfering) RNA such as micro RNA (miRNA) and short interfering RNA (siRNA), mitochondrial RNA (mtRNA), coding RNA, non-coding RNA, RNA having a sequence complimentary to a mutated or altered DNA including but not limited to translocated gene RNA and fusion gene RNA, RNA having a sequence complimentary to non-mutated DNA, mRNA splice variants, and ribonucleoprotein RNA.

According to an aspect of the invention, there is provided methods for detecting, diagnosing, inferring, evaluating or monitoring disease, particularly cancer or neoplastic disease in a human or animal, the method comprising the steps of isolating a predominately non-cellular or acellular fraction of a bodily fluid obtained from a human or animal, wherein the non-cellular fraction may be plasma, serum, or other non-cellular (acellular) bodily fluid; thereafter extracting RNA from the non-cellular fraction of the bodily fluid, such as from plasma, serum or other non-cellular bodily fluid specimen of a human or animal, wherein the extracted RNA may comprise total RNA or a heterogeneous mixture of RNA species or specific RNA species, determining quantitatively or qualitatively the amount or concentration of at least two RNA species from a fraction of said plasma, serum or other non-cellular bodily fluid fraction, wherein quantitative or qualitative determination of the amount or concentration of said RNA species thereby detects, diagnoses, infers, or monitors or enables evaluation of a cancer or neoplastic disease or other disease or condition in a human or animal. In a particularly preferred embodiment, at least two of the RNA species are tumor-associated RNA, and cancer or neoplastic disease is detected, diagnosed or inferred or evaluated when the relative or absolute amount or concentration of at least one RNA species from the plasma, serum or non-cellular bodily fluid fraction from a human or animal is greater than the amount or concentration of another RNA species from the plasma, serum, or non-cellular bodily fluid fraction from said human or animal. In one aspect of this embodiment, the RNA is a translocated gene or fusion gene RNA. In another particularly preferred embodiment, at least two of the RNA species are tumor-associated RNA and a third RNA species is not cancer-specific, and cancer or neoplastic disease is detected, diagnosed or inferred or evaluated when the relative or absolute amount or concentration of a least two of the tumor-associated RNA species from the plasma, serum, or non-cellular bodily fluid fraction of a human or animal is greater than the amount or concentration of the non-tumor specific RNA species in the plasma, serum, or non-cellular bodily fluid fraction from said human or animal. In another preferred embodiment, at least two of the RNA species are disease-specific, and the disease is diagnosed, detected, inferred, evaluated, characterized, or monitored in a human or animal when the relative or absolute amount or concentration of at least one RNA species from the plasma, serum, or non-cellular bodily fluid fraction is greater than the amount or concentration of another RNA species from the plasma, serum, or non-cellular bodily fluid fraction from said human or animal. In one aspect of this embodiment, the RNA is a translocated gene RNA or a fusion gene RNA. In another preferred embodiment, at least two of the RNA species are disease-specific RNA and a third RNA species is not disease-specific, and a disease is detected, diagnosed or inferred or evaluated when the relative or absolute amount or concentration of a least two of the disease-specific RNA species from the plasma, serum, or non-cellular bodily fluid fraction of a human or animal is greater than the amount or concentration of the non-disease specific RNA species in the plasma, serum, or non-cellular bodily fluid fraction from said human or animal.

In another preferred embodiment, a cancer or neoplastic disease is detected, diagnosed or inferred or evaluated when at least one extracellular RNA species are detected in the plasma, serum, or a bodily fluid of a human or animal, wherein at least one RNA is a translocated gene RNA or a fusion gene RNA.

According to another aspect of the present invention, there is provided methods for detecting, diagnosing, inferring, evaluating or monitoring disease, particularly cancer or neoplastic disease in a human or animal, the method comprising the steps of extracting total extracellular RNA from plasma or serum or other bodily fluid specimen of the human or animal (test specimen), determining quantitatively or qualitatively the amount or concentration of one or a plurality of extracellular RNA species from a fraction of said test specimen, and comparing said amount or concentration of one or a plurality of extracellular RNA species obtained from the fraction of said specimen to the amount or concentration of one or a plurality of corresponding extracellular RNA species in reference group specimen. In one aspect said comparison to the reference group provides either a numerical or positive/negative assessment of each extracellular RNA species within the test specimen compared to the reference specimen, and thereafter comparison of the numerical or positive/negative values thereby ascribed to each RNA species from the test specimen to values of other RNA species within the test specimen is made, wherein said comparison or patterns determined thereby detects, diagnoses, infers, or monitors a cancer or neoplastic disease in a human or animal. In preferred embodiments, the reference group is a human or human population of individuals without cancer. In alternative preferred embodiments, the reference group is a human or human population of individuals with cancer. In one aspect of this embodiment, one or more tumor-associated RNA is a translocated gene RNA, including a fusion gene RNA. In another aspect of this embodiment, one or more RNA are siRNA or miRNA. In another aspect of this embodiment, one or more RNA are mRNA targets of a siRNA or miRNA.

According to another aspect of the present invention, there are provided methods for detecting, diagnosing, inferring, evaluating or monitoring cancer or neoplastic disease in a human or animal, the method comprising the steps of obtaining a plasma or serum specimen from the human or animal, determining directly on a portion of said specimen the amount or concentration of total extracellular RNA or of one or more RNA species within a portion of the plasma or serum specimen, comparing said amount or concentration to that of a reference group, wherein said comparison thereby detects, diagnoses, infers, or monitors a cancer or neoplastic disease in a human or animal. In preferred embodiments, the reference group is a human or human population of individuals without cancer, and cancer or neoplastic disease is detected, diagnosed or inferred when the amount or concentration of total extracellular RNA in the fraction of the specimen is greater than the amount or concentration of total extracellular RNA found in the reference group, or when one or more RNA species in the fraction of the specimen is greater than the amount or concentration of said species found in the reference group. In alternative preferred embodiments, the reference group is a human or human population of individuals with cancer, and cancer or neoplastic disease is detected, diagnosed or inferred when the amount or concentration of total extracellular RNA or one or more RNA species in the fraction of the specimen is not significantly less than the amount or concentration of total extracellular RNA found in the reference group. In an alternative preferred embodiment, the amount or concentration of one or more RNA species may be less than that of the reference group, whereby cancer or neoplastic disease is thereby detected, diagnosed, inferred, evaluated, or characterized. In one aspect of this embodiment, an extracellular messenger RNA is less than that of a reference group and an extracellular inhibitory RNA is greater than that of a reference group. In one aspect of this embodiment, one or more tumor-associated RNA is a translocated gene RNA. In one aspect of this embodiment, one or more tumor-associated RNA is a fusion gene RNA. In another aspect of this embodiment, one or more RNA are siRNA or miRNA. In another aspect of this embodiment, one or more RNA are mRNA targets of a siRNA or miRNA.

It is to be recognized within the scope of this invention that the amounts, concentrations, values, or ratios of one or more RNA species, DNA species, proteins, total extracellular RNA levels, or total extracellular DNA levels for a reference group or specimen may be pre-defined, and standard values or baseline values provided or utilized within the scope of the embodiments of the invention. Further, pre-defined standard values or baseline values may include a reference range to determine normal or abnormal values, and may include standards of deviation, confidence level determinations, and adjusted or pre-defined ranges or values based upon age, sex, race, or other specific parameters. Further, there may be provided a control specimen, including a control bodily fluid or control RNA, DNA, or protein, or control synthetic construct, that enables re-calibration of the pre-defined reference values or baselines based upon testing.

It is to be recognized as a particularly preferred embodiment, and within the scope of the invention, that qualitative or quantitative analysis of multiple RNA species from plasma, serum, or other non-cellular bodily fluid fraction, enables determination of a RNA pattern or RNA expression profile or RNA signature, wherein said pattern, profile, or signature thereby enables the diagnosis, detection, evaluation, characterization, or monitoring of a cancer, neoplastic disease, or other disease. In one aspect, said RNA pattern, RNA expression profile or RNA signature is analyzed visually, statistically, or mathematically, against a known or standard RNA pattern, expression profile, or signature, of a reference group or specimen with or without cancer, neoplastic disease, or other disease of interest. It is further to be recognized that the reference group or specimen(s) RNA pattern, expression profile, or signature, may be specific to a particular cancer or be intended to encompass various cancer types.

In a preferred embodiment of the inventive methods, the bodily fluid is blood, plasma, serum, urine, effusions including pleural effusions, ascitic fluid, saliva, cerebrospinal fluid, gastrointestinal secretions, bronchial secretions including sputum, cervical secretions, or breast secretions. In a particularly preferred embodiment, the bodily fluid is plasma or serum. In particularly preferred embodiments of the inventive methods, the non-cellular (acellular) bodily fluid or bodily fluid fraction is blood plasma or serum. Other predominately non-cellular (acellular) bodily fluids particularly include urine, saliva, and cerebrospinal fluid, and may further include certain gastrointestinal secretions and transudates.

In preferred embodiments a predominately non-cellular fraction of a bodily fluid is isolated by obtaining a bodily fluid from a human or animal and centrifuging the bodily fluid to isolate a predominately non-cellular fraction of a bodily fluid. In another preferred embodiment, a predominately non-cellular fraction of a bodily fluid is isolated by obtaining a bodily fluid from a human or animal and passing the bodily fluid through a filter of sufficient size to separate the cellular and non-cellular fractions of the bodily fluid, or otherwise size-fractionate the bodily fluid, and thereby isolate the non-cellular fraction of a bodily fluid. In particularly preferred aspects of these embodiments, plasma or serum is isolated from blood. Further, predominately non-cellular bodily fluids, including but not limited to urine, saliva, and cerebrospinal fluid may be further purified by process of centrifugation, or filtering or size-fractionation, or analyzed without further purification.

In preferred embodiments of the inventive methods, the amount of total extracellular RNA, or one or a plurality of extracellular RNA species, is determined quantitatively or qualitatively using a method that is nucleic acid amplification, signal amplification, spectroscopy including mass spectroscopy, or hybridization, preferably to a detectably-labeled probe.

In preferred embodiments of the inventive methods, RNA is extracted from blood, plasma, serum, or other bodily fluid using an extraction method that is a gelatin extraction method; a silica, glass bead, or diatom extraction method; guanidinium thiocyanate acid-phenol based extraction methods; guanidinium thiocyanate acid based extraction methods; phenol-chloroform based extraction methods; by centrifugation through a cesium chloride or similar gradient; or using commercially-available RNA extraction methods, most preferably as provided in a kit comprising instructions from the kit manufacturer.

In preferred embodiments of the invention, RNA extracted from plasma, serum, or other bodily fluid is reverse transcribed to cDNA prior to hybridization and detection or hybridization, amplification and detection. In these embodiments, the amount or concentration of RNA is determined by qualitative or quantitative analysis of cDNA or amplified cDNA product or amplified signal.

In preferred embodiments of the invention, extracted RNA or the corresponding cDNA is amplified qualitatively or quantitatively to determine the amount or concentration of a RNA species, using an amplification method that is, for example, polymerase chain reaction, or reverse transcriptase polymerase chain reaction; ligase chain reaction; DNA or RNA signal amplification; amplifiable RNA reporter methods; Q-beta replication; transcription-based amplification; isothermal nucleic acid sequence based amplification; self-sustained sequence replication assays; boomerang DNA amplification; strand displacement activation; cycling probe technology; and any combination or variation thereof.

In preferred embodiments of the inventive methods, detection of amplified RNA or cDNA product is performed using a detection method that is, for example, gel electrophoresis; enzyme-linked immunosorbent assay (ELISA), including embodiments comprising biotinylated or otherwise modified amplification primers; hybridization using a specific, detectably-labeled probe, for example, a fluorescent-, radioisotope-, or chromogenically-labeled probe; Southern blot analysis; Northern blot analysis; electrochemiluminescence; reverse dot blot detection; high-performance liquid chromatography; and variations thereof.

The methods of the invention particularly provide methods for identifying humans at risk for developing a disease, particularly cancer or other neoplastic disease, or who have a malignancy or premalignancy. The methods of the invention thus provide methods for identifying humans having a malignancy such as but not limited to breast, ovarian, lung, cervical, colorectal, gastric, prostate, pancreatic, bladder, endometrial, head & neck, brain, kidney, or esophageal cancers, leukemias, lymphomas, melanoma, or sarcomas; and premalignancies including but not limited to colorectal adenoma, cervical dysplasia, cervical intraepithelial neoplasia (CIN), bronchial dysplasia, atypical hyperplasia of the breast, ductal carcinoma in-situ, atypical endometrial hyperplasia, myelodysplastic syndromes, myeloproliferative syndromes, and Barrett's esophagus.

The invention thus permits the presence of cancerous (malignant) or pre-cancerous (premalignant) cells within a human or animal to be detected or inferred by determining an amount or concentration of RNA in the plasma, serum, or other bodily fluid of said human or animal that exceeds the amount or concentration normally present in the plasma, serum, or other bodily fluid of a human or animal without cancer or pre-malignancy.

The invention also permits the existence of a disease within a human or animal to be detected or inferred by determining an amount or concentration of RNA in the plasma, serum, or other bodily fluid of said human or animal that exceeds the amount or concentration normally present in the plasma, serum, or other bodily fluid of a healthy human or animal.

An advantageous application of this invention is to identify humans or animals with disease.

It is a particularly advantageous application of this invention to identify humans or animals having cancer.

Another advantageous application of this invention is to identify humans or animals having risk for developing cancer.

Another advantageous application of this invention is to identify humans or animals having a premalignant disease or condition.

Another advantageous application of this invention is for monitoring cancer, including response to cancer therapies, including surgery, biotherapy, hormonal therapy, anti-sense therapy, monoclonal antibody therapy, chemotherapy, vaccines, anti-angiogenic therapy, cryotherapy, radiation therapy, and therapies based upon or directed at inhibitory RNA or regulatory RNA, including siRNA and miRNA.

Another advantageous application of this invention is selecting humans or animals for cancer therapies, including surgery, biotherapy, hormonal therapy, anti-sense therapy, monoclonal antibody therapy, chemotherapy, vaccines, anti-angiogenic therapy, cryotherapy, radiation therapy, and therapies based upon or directed at inhibitory RNA or regulatory RNA, including siRNA and miRNA.

Another advantageous application of this invention is to provide a marker as a guide to whether adequate therapeutic effect has been achieved, or whether additional or more advanced therapy is required, and to assess prognosis in a patient.

Another advantageous application of this invention is to provide an indicator of a relapsed cancer following therapy, or impending relapse, or treatment failure.

Another advantageous application of this invention is to identify humans or animals who might benefit from additional diagnostic procedures, wherein said procedures include but are not limited to surgery, biopsy, needle aspiration, radiologic imaging including X-ray, MRI, and CT scanning, radionucleotide imaging, colonoscopy, sigmoidoscopy, bronchoscopy, endoscopy, PET scanning, stool analysis, sputum analysis, cystoscopy, pelvic examination, and physical examination.

The invention further provides kits that provide stabilizing agent for use in combination with plasma, serum, or bodily fluid to stabilize extracellular RNA within said plasma, serum, or bodily fluid.

The invention also provides diagnostic kits enabling quantitative or qualitative assessment of total RNA or specific RNA species in plasma or serum, wherein a reference range for normal values or cancer values is provided to enable identification or selection of a human or animal with or at risk for cancer.

A particular advantage of this invention is detection of an extracellular translocated gene RNA or fusion gene RNA in plasma or serum or other bodily fluid of a human or animal.

A particular advantage of this invention is the diagnosing, detection, evaluation, or monitoring of neoplastic disease in a human or animal by detecting extracellular tumor-associated translocated gene RNA or fusion gene RNA in plasma or serum or other bodily fluid of said human or animal.

Specific preferred embodiments of the present invention will become evident from the following more detailed description of certain preferred embodiments and the claims.

DETAILED DESCRIPTION OF THE INVENTION

This invention relates to methods for detecting tumor-associated RNA in plasma, serum and other bodily fluids. The methods thereby provide for the detecting, diagnosing, inferring, evaluating or monitoring of cancer or neoplastic disease in a human or animal. The inventive methods comprise the steps of extracting RNA from plasma, serum, or bodily fluid of a human or animal, and thereafter assessing the amount or concentration of mammalian extracellular RNA in said plasma, serum, or other bodily fluid of the human or animal, or cDNA derived therefrom. Particularly preferred embodiments of the inventive steps include an amplification or signal amplification step, followed by detection of the amplified product or signal. In particularly preferred embodiments this is performed by comparing the amount or concentration of one or more RNA species in said plasma, serum, or bodily fluid obtained from the human or animal with another, or with the amount or concentration of RNA found in bodily fluid from a reference individual, group or population of known disease status. In particular, the invention provides methods for detecting, inferring, evaluating or monitoring the presence of cancerous or precancerous cells in a human or animal, whether from a non-hematologic neoplasm (i.e., a solid-tumor) or from a hematologic malignancy (such as leukemia, lymphoma, myeloma, etc.). Although extracellular RNA has demonstrated sufficient stability in plasma, serum and other bodily fluid to permit performance of the inventive methods, in optional methods of the invention in the first step stability of the extracellular RNA in plasma, serum or bodily fluid may be enhanced by combining plasma, serum, or bodily fluid with an agent that protects or stabilizes RNA from degradation by RNase, herein referred to as stabilizing agent, and thereafter in the next step or steps determine an amount, concentration or other quantitative or comparative assessment of RNA from a bodily fluid specimen obtained from a human or animal, wherein the RNA can be either total extracellular RNA, or one or a plurality of specific RNA species or multiple specific RNA species. RNA species may be either tumor-related RNA or non-tumor related RNA. Total extracellular RNA will be recognized as comprising both tumor-related (tumor-associated) and non-tumor-related (non-tumor-associated) RNA when obtained from a patient with cancer or other neoplastic disease. In preferred embodiments, the bodily fluid is blood, plasma, serum, urine, effusions including pleural effusions, ascitic fluid, saliva, cerebrospinal fluid, gastrointestinal secretions, bronchial secretions The methods of the invention in the first step isolate a predominately non-cellular fraction of a bodily fluid obtained from a human or animal, wherein the non-cellular bodily fluid fraction may be plasma, serum, or other bodily fluid. In preferred embodiments, a non-cellular fraction is isolated by centrifugation of a cellular bodily fluid such as blood, or by other means known to the art such as but not limited to by passing the bodily fluid through a filter or otherwise size fractionating or density fractionating to separate the bodily fluid, whereby the cellular and non-cellular components of the bodily fluid are separated and the non-cellular fraction of the bodily fluid is thereby isolated. In particular preferred embodiments, plasma or serum is isolated from whole blood. Serum is obtained by allowing blood to clot, and may thereafter by isolated or further purified by methods known in the art or described herein. It is recognized that the non-cellular fraction of a bodily fluid may pass through multiple steps to further purify or isolate a non-cellular fraction, for example by differential centrifugation, or by combining centrifugation with filtering or size exclusion, or weight/density separation. Furthermore, it will be recognized that some bodily fluid such as transudates, saliva, urine, and cerebrospinal fluid may be predominately non-cellular, whereby a predominately non-cellular fraction of bodily fluid may be obtained by obtaining the bodily fluid from a human or animal. It is further to be recognized that predominately non-cellular bodily fluids may be further purified by centrifugation, filtering, or size-fractionation of the non-cellular fluid. It is to be recognized herein that plasma and serum are considered bodily fluids, and further are considered to be non-cellular fractions of a bodily fluid being blood. including sputum, cervical secretions, or breast secretions. Plasma and serum are particularly preferred bodily fluids, but any bodily fluid a portion of which comprises extracellular RNA, and particularly tumor-associated extracellular RNA is useful in the practice of the methods of this invention. It is further recognized herein that extracellular tumor-associated RNA or disease-associated RNA may be extracted directly from whole blood or other cellular bodily fluid without prior separation of the non-cellular bodily fluid fraction. In particular, it is recognized that certain disease states, for example but not limitation, in premalignant disease and conditions, cancerous or diseased cells are not anticipated to circulate in blood, and therefore tumor-associated or disease-associated RNA extracted from whole blood or other cellular bodily fluid will be recognized to have been primarily extracellular RNA in these disease states or conditions. Similarly, in early stages of cancer, the extracellular RNA component in blood could be expected to dominate.

As used herein, the terms "tumor-associated," "disease-associated", "disease-related,""tumor-related" and "non-tumor-related" are intended to characterize particular RNA species that comprise a fraction of total extracellular RNA. It will be understood that certain RNA species are recognized in the art as being associated with the existence of cells comprising a disease state, particularly neoplastic disease, malignancy or premalignancy. RNA species are "tumor-associated", "disease-associated," "disease-related," "tumor-related"when their presence or level as a component of total extracellular RNA is indicative of the existence of a disease, particularly a neoplastic disease, and/or when it has been shown that said RNA species are over-expressed in diseased cells or tissue in comparison to the non-diseased state. It will be recognized that in certain embodiments of the methods of this invention, detecting a comparative lack of expression of an RNA species may further indicate the existence of disease in said human or animal when under-expression of said RNA species is characteristic of said disease state in comparison to the healthy state.

As used herein, the term "RNA species" refers to RNA selected from one or more of the group comprising messenger RNA (mRNA), transfer RNA (tRNA), ribosomal RNA (rRNA), mitochondrial RNA (mtRNA), inhibitory or interfering RNA such as short interfering RNA (siRNA) or micro RNA (miRNA), coding RNA, non-coding RNA, RNA having a sequence complimentary to a mutated or altered DNA, RNA having a sequence complimentary to non-mutated DNA, ribonucleoprotein RNA, and messenger RNA splice variants. It is understood herein that RNA species may further be disease-associated, tumor-associated, disease-related, tumor-related, and non-tumor-related. In particular preferred aspects of the invention, tumor-associated RNA are translocated gene RNA and/or fusion gene RNA.

Neoplastic diseases include both cancer and premalignant diseases and conditions. The inventive steps are applicable to cancers well known in the art, including but not limited to hematopoietic cancers and malignancies including acute leukemia (including acute myelogenous leukemia, and acute lymphocytic leukemia), chronic leukemia (including chronic lymphocytic leukemia and chronic myelogenoous leukemia), lymphoma (including Non-Hodgkins lymphoma and Hodgkins lymphoma), multiple myeloma and other plasma cell and lymphoplasmacytic neoplasms; solid tumor cancers and malignancies, including cancers of the breast, ovary, lung (including non-small cell lung cancer and small cell lung cancer), bronchial, pleural, colorectal, liver, gallbladder and biliary ducts, cervix, gastric, pancreas, bladder, uterus (including endometrial), brain, testes, kidney, esophagus, skin (including malignant melanoma), head & neck, thyroid, sarcomas, and cancer of unknown primary; hematopoeitic premalignant diseases and conditions, including myelodysplastic syndrome and preleukemia, myeloproliferative disorders (including polycythemia vera and myelofibrosis), primary thrombocythemia; and solid-tumor premalignant diseases and conditions, including colorectal adenoma, cervical dysplasia, cervical intraepithelial neoplasia (CIN), bronchial dysplasia and metaplasia, stypical hyperplasia of the breast, ductal carcinoma in-situ, atypical endometrial hyperplasia, prostatic intraepithelial neoplasia (PIN), and Barrett's esophagus.

Qualitative or quantitative determination of the amount or concentration of one or more RNA species from said human or animal bodily fluid specimen is made in comparison to another RNA species from said specimen, or to total RNA, extracellular DNA, or extracellular protein from said specimen, or to a standard amount, concentration The reference set of values or standards may include standard deviations, confidence intervals, ranges based upon age, sex, race, disease stage or condition, disease characteristic, prior treatment characteristics, or other parameters. Assessment of the relative or absolute concentration or amount of extracellular RNA species in a non-cellular bodily fluid from a human or animal to the amount or concentration of said RNA species in said bodily fluid from a reference individual, group, or population or specimen or other standard thereby enables determination of the likelihood that the subject human or animal has a disease. In one aspect a disease such as cancer or neoplastic disease such as premalignancy is determined or evaluated, wherein if the amount or concentration of one or a plurality of specific RNA species from the non-cellular bodily fluid fraction of the subject human or animal is demonstrated to be either greater than or less than the amount or concentration present in individuals, groups, or populations without disease, then a disease (for example, cancer) or an increased risk of disease, or value or set of values from a reference individual, group, population or specimen (for example, due to the existence of a premalignancy) will be inferred in the human or animal subject. Similarly, if the amount or concentration of total extracellular RNA, or of one or a plurality of specific RNA species thereof in the bodily fluid of the subject is within the range of a group or population with a disease, particularly cancer or neoplastic disease such as a premalignancy, then a disease, particularly cancer or an increased risk of cancer (for example, due to the existence of a premalignancy) will be inferred in the human or animal subject. If the amount or concentration of total extracellular RNA, or of one or a plurality of specific RNA species thereof in the bodily fluid of the subject is less than the range for patients with cancer, or within the range of the healthy population, then the risk of disease, particularly cancer or an increased risk of cancer (for example, due to the existence of a premalignancy) will be less. It will be recognized that the limits of the reference range values may be set in a manner that determines a sensitivity or specificity or positive predictive value or negative predictive value for the assay, or otherwise provides the probability of the assay correctly identifying a subject with cancer or neoplasm. Thus, in this manner the reference range for a group or population can be defined that increases the sensitivity or specificity of the assay.

It will also be recognized that lower concentrations of some extracellular RNA species relative to the reference group may be indicative of higher risk of malignancy.

It is to be recognized that a variety of individuals, groups, or populations will provide suitable reference values that enable discrimination of abnormal (disease-, and more particularly cancer-, related) and normal amounts or concentrations of total extracellular RNA, or of one or a plurality of specific RNA species thereof in the bodily fluid of the subject. Appropriate reference individuals, groups, or populations include but is not limited to: a healthy human or animal, more specifically a human or animal population without neoplastic disease (cancer or premalignancy) or a human or animal population without cancer; a human or animal population with a disease, more specifically a human or animal population with neoplastic disease (cancer or premalignancy) or a human or animal population with cancer; a previously-isolated bodily fluid specimen from the human or animal under evaluation corresponding to a known disease or health state. In addition, it will be recognized that certain defined groups or populations will provide useful reference values to assess probability of disease, particularly cancer or premalignancy, in a subject, including but not limited to: groups and populations defined by gender and the presence or absence of disease, particularly cancer or premalignancy; groups and populations defined by race or ethnicity and presence or absence of disease, particularly cancer or premalignancy; groups and populations defined by non-neoplastic diseases; groups and populations defined by specific tumor types; groups and populations defined by stage or extent of cancer of a particular type; groups and populations defined by certain environmental or occupational risks for cancer, such as smokers or workers occupationally exposed to carcinogens; and groups and populations defined by genetic or family risk for cancer. It is to be understood that the comparative assessment of the subject's extracellular RNA species of interest, or the subject's total extracellular RNA in a bodily fluid such as blood plasma or serum to reference groups and populations may be made by either non-statistical or statistical analysis, as is known to the art.

It is further to be understood that quantitative or qualitative analysis of multiple extracellular RNA species from a non-cellular bodily fluid of a human or animal enables determination of a RNA pattern or RNA expression profile or RNA signature, wherein said pattern, profile, or signature thereby enables the diagnosis, detection, evaluation, characterization, or monitoring of a cancer, neoplastic disease, or other disease of interest. The resultant RNA pattern, RNA expression profile, or RNA signature may be analyzed visually, statistically, or otherwise mathematically against the known RNA pattern, RNA expression profile, or RNA signature of a reference group or specimen having or not having the cancer, neoplastic disease, or disease of interest. The reference group or specimen RNA pattern, RNA expression profile, or RNA signature may be specific to a particular cancer, or be intended to encompass various cancer types.

In particularly preferred embodiments of the invention, one or more RNA species present in plasma, serum, or non-cellular fraction of a bodily fluid of a human or animal is quantitatively or qualitatively assessed relative to one or more other RNA species within said plasma, serum, or non-cellular fraction of a bodily fluid, whereby comparative assessment of said RNA species is made by either non-statistical or statistical analysis, as known in the art. Comparative analysis of two or more extracellular RNA species in plasma, serum, or other bodily fluid thereby provides methods for detecting, inferring, characterizing, evaluating, or monitoring cancer or premalignancy. In one optional step of this embodiment, the invention in the first step stabilizes the extracellular RNA in plasma, serum, or bodily fluid by combining RNA plasma, serum, or bodily fluid with an agent that protects or stabilizes RNA from degradation by RNase, herein referred to as stabilizing agent, and thereafter in the next step or steps is determined an amount, concentration, or other quantitative or comparative assessment of the RNA species of interest. Comparative assessment may be accomplished by extracting total RNA from the plasma, serum, or bodily fluid; amplifying or signal amplifying either sequentially or concurrently and in a qualitative or quantitative fashion the RNA species of interest, or cDNA derived therefrom, comprising a fraction of the extracted RNA; detecting the amplified products or amplified signal of the RNA species or cDNA derived therefrom; whereby detection, diagnosis, evaluation, characterization, or monitoring of cancer or premalignancy is thereby accomplished.

In another aspect of the preferred embodiment, comparative analysis of two or more extracellular RNA species from plasma, serum, or bodily fluid is accomplished without the step of providing the stabilizing agent to plasma, serum, or bodily fluid. In this aspect of the preferred embodiment, total RNA is extracted from plasma, serum, or bodily fluid; amplifying or signal amplifying in a qualitative or quantitative fashion and in a sequential or concurrent manner, two or more RNA species or cDNA derived therefrom, comprising a fraction of the extracted RNA; detecting the amplified or signal amplified product; whereby cancer or premalignancy is detected, diagnosed, evaluated, characterized, or monitored. In preferred embodiments, one or more of the RNA species is a fusion gene RNA.

In particularly preferred embodiments of the invention, the bodily fluid is blood plasma or serum. Either fresh (i.e., never frozen) blood plasma or serum, or frozen (stored) and subsequently thawed plasma or serum may be used for purposes of these embodiments. In a preferred embodiments the blood is processed soon after drawing, preferably within 48 hours and most preferably within 24 hours, to minimize any degradation of nucleic acids. While early processing is not a requirement of the methods of the invention, it will be recognized that variations of early processing can be employed as set forth below, without limitation implied. In one aspect, the blood may be initially processed to stabilize the RNA or to stabilize phospholipids encapsulating the extracellular RNA, or to inhibit nucleases present in blood. Stabilizing agents or inhibitors may be provided within kits according to the invention or within venipuncture tubes or devices. Such initial processing is useful if specimen transport or work schedules will result in processing delays. In another aspect, initial processing may be performed by hybridizing the RNA or binding associated apoptotic bodies or other RNA encapsulated particles to solid substrates shortly after venipuncture, preferably using reagents provided in a kit of this invention or as part of specialized blood collection systems. It is preferred that the processing of the specimen from the human or animal subject and from the reference group or population be handled in a similar or like manner to the extent practical, or alternatively the effect due to variations in specimen processing defined and comparisons appropriately adjusted.

In a preferred embodiment, blood is first collected by venipuncture and may be kept on ice until serum or plasma is separated from whole blood, for example using centrifugation methods preferably gentle enough not to cause lysis or disruption of blood cells. While a considerable range of centrifugation speeds may be employed, centrifugation at high speeds (such as beyond $100,000 \times g$) for prolonged periods should be avoided to prevent clearance of RNA-containing apoptotic bodies or other encapsulated extracellular RNA particles from the supernatant. Non-limiting examples of suitable conditions is centrifuging a blood specimen at a range of 300 to $5,000 \times g$ for five to thirty minutes, or fractionating by other standard methods to produce plasma or serum will suffice. Sera or plasma obtained in this manner can be assayed directly or stored frozen, for example but not limitation at $-20$ to $-80$ degrees centigrade until further analysis according to the methods of this invention.

In a preferred embodiment of the invention, extracellular RNA in plasma or serum or other bodily fluid of the human or animal is assayed by extracting total extracellular RNA from plasma or serum or other bodily fluid of the human or animal, determining quantitatively or qualitatively the amount or concentration of total extracellular RNA, or one or a plurality of specific RNA species thereof comprising a portion of the total extracellular RNA, and comparing said amount or concentration obtained from the human or animal to the total extracellular RNA, or one or a plurality of specific RNA species thereof from a reference group, wherein said comparison detects, diagnoses, infers, or monitors a disease, particularly cancer or neoplastic disease in the human or animal. Bodily fluids are preferably separated into essentially cellular and non-cellular components, using centrifugation or other fractionation techniques, and total extracellular RNA thereafter extracted from the non-cellular components.

In the practice of the methods of this invention, total extracellular RNA can be extracted from bodily fluid using methods well-known to the art, including but not limited to gelatin extraction method; silica, glass bead, or diatom extraction method; guanidinium thiocyanate acid-phenol based extraction methods; guanidinium thiocyanate acid based extraction methods; centrifugation through a cesium chloride or similar gradient; phenol-chloroform based extraction methods; hybridization and immunobead separation; or commercially available RNA extraction methods. Methods of RNA extraction are further provided in U.S. Pat. No. 6,329,179 B1, incorporated herein in its entirety by reference. If plasma or serum had been previously frozen, upon assay it is preferred that it be thawed rapidly, for example in a warm water bath at about 37 degrees centigrade, and thereafter RNA rapidly extracted to minimize degradation thereof.

However, it should be understood that extraction of total extracellular RNA is not a requirement for the practice of the methods of this invention. In some embodiments, methods such as spectroscopic methods including mass spectroscopy, and cytometry can be used for direct analysis of total extracellular RNA or RNA encapsulated particles within the bodily fluid.

The amount or concentration of total extracellular RNA from the bodily fluid is determined quantitatively or qualitatively using nucleic acid (RNA or cDNA) amplification, signal amplification, spectroscopy including mass spectroscopy, or hybridization to a detectably-labeled probe. In a preferred embodiment, a portion of the extracted total extracellular RNA is amplified or signal amplified qualitatively or quantitatively. Methods of RNA (or cDNA derived therefrom) amplification are further provided in U.S. Pat. No. 6,329,179 B1, incorporated herein in its entirety by reference.

Total extracellular RNA extracted from blood plasma or serum or other bodily fluid may first be reverse transcribed to cDNA, whereupon the cDNA is amplified or signal amplified qualitatively or quantitatively. In preferred embodiments, amplification is performed using primers or probes that are specific for particular RNA or cDNA species, wherein the RNA or its cDNA may be a non-tumor related RNA or a tumor-related RNA. Non-tumor RNA include but are not limited to housekeeper gene RNA, and non-limiting examples of non-tumor RNA include RNA encoding all or a portion of c-abl, porpho-bilinogen deaminase (PBDG), glyceraldehyde 3-phosphate dehydrogenase (GAPDH), retinoic acid receptor (RAR), and beta-actin. Examples of tumor-related or tumor-associated RNA not intending to be limiting include tyrosinase RNA, keratin RNA species, prostate specific antigen RNA, alpha-fetoprotein RNA, bcr-abl RNA, carcinoembryonic antigen RNA, p97 RNA, p16 RNA, MUC 18 RNA, PML/RAR RNA, CD44 RNA, EWS/FLI-1 RNA, EWS/ERG RNA, AML1/ETO RNA, MAGE RNA species, beta human chorionic gonadotropin RNA, telomerase-associated RNA including TEP1 RNA, human telomerase RNA template (hTR) RNA and telomerase reverse transcriptase protein (hTERT) RNA, bcl-2 RNA, bax RNA, survivin RNA, COX-2 RNA, P53 RNA, c-myc RNA, her-2/neu RNA, Von Hippel-Lindau gene RNA, retinoblastoma gene RNA, mutated in colon cancer (MCC) gene RNA, adenomatous polyposis coli (APC) gene RNA, deleted in colon cancer (DCC) gene RNA, epidermal growth factor receptor (EGFR) RNA, mutated K-ras RNA, mutated N-ras RNA, mutated H-ras RNA, epidermal growth factor (EGF) RNA, hn RNP-A1 RNA, hn RNP-A2/B1 RNA, hn RNP-K RNA, 5T4 RNA, DNA methyltransferase RNA, matrix metalloproteinase species RNA, raf kinase RNA, mammaglobin RNA, DD3 (PCA3) RNA, JAK-2 RNA, polo-like kinase 1 (Plk1) RNA, neuropilin (NRP)-1 RNA, NRP-2 RNA, c-kit RNA, XIAP RNA, NPM RNA, CLLU1 RNA, Src RNA, BRCA-1 RNA, BRCA-2 RNA, glutathione S-transferase RNA, MDR-1 RNA, and JC virus RNA. It will be recognized that the above examples are not intended to be limiting, and any non-tumor or tumor-related RNA species or corresponding cDNA may be detected according to the methods of this invention. Further, it will be recognized that various RNA species are well known to the art, and that the scope of the invention is meant to encompass these RNA species without limitation. It will further be recognized that some RNA species will be recognized in the art to be tumor-associated when characterized by a mutation, (for example but not limitation, mutated oncogenes), or other nucleotide variation, including SNPs.

In particularly preferred embodiments of the invention, the tumor-associated RNA are translocated gene RNA and/or fusion gene RNA, wherein said tumor-associated RNA include but are not limited to bcl-2/IgH RNA, bcl-1/IgH RNA, bcr-abl RNA, PML/RAR RNA, AML1-ETO RNA, EWS/FLI-1 RNA, EWS/ERG RNA, ETS family gene fusion RNA, TMPRSS2/ERG RNA, TMPRSS2-ETV1 RNA, TEL-AML1 RNA, TMPRSS2-ETV4 RNA, C15orf21/ETS RNA, HNRPA2B1/ETS RNA, RET fusion gene RNA, NTRK1 fusion gene RNA, PAX8-PPARG RNA, MECT1-MAML2 RNA, ETV6-NTRK3 RNA, NPM-ALK RNA, EML4-ALK RNA, TPM3-ALK RNA, TFG-ALK RNA, ATIC-ALK RNA, PAX3-FKHR RNA, PAX7-FKHR RNA, ETV6-PDGFRB RNA, EWSR1-DDIT3 RNA, FUS-DDIT3 RNA, PCM1-JAK2 RNA, BCR-JAK2 RNA SS18-SSX RNA and JAZF1-JJAZ1 RNA.

In another preferred embodiment of the invention, the tumor-associated RNA is receptor tyrosine kinase-associated RNA, including but not limited to HER-2/neu RNA, epidermal growth factor receptor RNA (EGFR RNA), c-kit RNA, c-Met RNA, Flt-3 RNA, and platelet-derived growth factor receptors (PDGFR) RNA.

In another aspect of the invention, the tumor-associated RNA is a hormone receptor RNA, including but not limited to estrogen receptor RNA, progesterone receptor RNA, insulin and insulin-like growth factor-1 receptor RNA including IGF-1 RNA and IGFR-1 RNA, and guanylyl cyclase C (GCC) receptor RNA.

In another aspect of the invention, siRNA or miRNA-associated RNA include Dicer RNA, Drosha RNA, and RNA-induced silencing complex (RISC) ribonucleoprotein RNA.

Various amplification methods or signal amplification methods are known in the art and can be used in accordance with the methods of this invention. In preferred embodiments of the methods of the invention, quantitative or qualitative amplification is performed using an amplification or signal amplification method such as polymerase chain reaction; reverse transcriptase polymerase chain reaction; ligase chain reaction; DNA or RNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; or any combination or variation thereof. In one aspect of this embodiment, quantitative amplification is performed using the Taqman technology (Perkin Elmer Biosystems), with primers for the target RNA using a dye-labeled internal primer.

In preferred embodiments, following amplification the RNA or cDNA amplified or signal amplified product is detected in a quantitative or qualitative manner by methods known to the art. In preferred embodiments of the inventive methods, detection of amplified RNA or cDNA product is performed using a detection method selected from a group consisting of gel electrophoresis; ELISA detection including modifications, including biotinylated or otherwise modified primers; hybridization using a specific, fluorescent-, radioisotope-, or chromogenically-labeled probe; Southern blot analysis; Northern blot analysis; electrochemiluminescence; reverse dot blot detection; mass spectroscopy; and liquid chromatography, including high-performance liquid chromatography.

Upon amplification and detection of total extracellular RNA or one or a plurality of specific RNA species, most preferably wherein one or a plurality of species of total extracellular RNA is a disease- or tumor-related gene, an amount or concentration or other value allowing comparative assessment is determines, using for example, gel intensity, signal intensity, or color intensity, color, mass, or electrical propensity. Assessment is made to a reference individual, group, or population based upon analysis of said RNA under similar condition and methods, or by extrapolation to similar conditions and methods. If the RNA in the subject specimen is of greater amount, concentration, or other assessment value than that expected for a healthy reference group or population, or within the range for a disease group or population, most preferably a cancer group or population, then disease, most particularly cancer or neoplastic disease, will be thereby diagnosed, detected, inferred, or monitored in the subject human or animal.

In another embodiment of the invention, determination of an amount, concentration, or other comparative assessment is made using total extracellular RNA without amplification prior to detection. For example but not limitation, total extracellular RNA extracted from a bodily fluid may be hybridized and detected without amplification. In this aspect, it is particularly preferred but not required that the extracted RNA be concentrated upon extraction or upon separation from the bodily fluid, using for example immunobead capture or hybridization onto a solid substrate, to improve assay sensitivity. In another aspect of this embodiment, extracellular RNA is evaluated by spectroscopy, for example by mass spectroscopy or magnetic resonance spectroscopy, or by flow cytometry. In one aspect, fluorometric methods may be employed, for example as employed by Kamm and Smith (1972, *Clin. Chem.* 18: 519-522), said reference incorporated herein in its entirety.

The methods of the invention identify humans or animals bearing or at risk for developing malignancies including but not limited to tumors of breast, ovarian, lung, cervical, colorectal, gastric, pancreatic, bladder, endometrial, head and neck, brain, kidney, and esophageal tissues, as well as leukemias, lymphomas, melanoma, and sarcomas. The methods of the invention may further be utilized to identify humans or animals with premalignancy, including but not limited to colorectal adenoma, cervical dysplasia, cervical intraepithelial neoplasia (CIN), bronchial dysplasia, bronchial metaplasia, atypical hyperplasia of the breast, ductal carcinoma in-situ of the breast, atypical endometrial hyperplasia, prostatic intraepithelial neoplasia, and Barrett's esophagus. The methods of the invention may be applied to a subject of any age, race, ethnicity or gender, although it is preferred that the reference group or population include individuals of similar age (child, adult, elderly) and sex (male, female).

The invention permits detection, diagnosis, and monitoring of disease, particularly cancer and premalignancy, and identification of individuals at risk for developing disease, particularly cancer or neoplastic disease such as premalignancy, providing considerable clinical utility. The invention provides methods to identify, stratify, or select a human or animal that might benefit from a therapy, or from a further diagnostic test. The invention permits disease such as cancer to be monitored, including response to cancer therapies, by providing a marker to guide whether therapeutic effect has been achieved, or if more therapy is required, and to assess prognosis.

An advantageous application of the methods of this invention is to allow selection of humans or animals for cancer therapies including surgery, biotherapy, hormonal therapy, anti-sense therapy, monoclonal antibody therapy, chemotherapy, vaccines, anti-angiogenic therapy, cryotherapy, radiation therapy, and RNA inhibitor-directed therapies.

A particularly advantageous application of the invention is for selection and monitoring of receptor tyrosine kinase inhibitor therapies. In one aspect of this embodiment, the cancer therapy is a pharmaceutical product that inhibits, blocks, or interferes with the tyrosine kinase pathway or with tyrosine kinase-associated receptors. In one aspect, the pharmaceutical product inhibits, blocks, or interferes with HER-2/neu, EGFR, c-Kit, Flt-3, c-Met or PDGFR.

In one advantageous application, the invention provides for the monitoring of RNA inhibitor therapies, including but not limited to anti-sense therapies and siRNA therapies, wherein the therapy is monitored by the monitoring of an extracellular mRNA species corresponding to an mRNA species that is the target of the therapy.

Another advantageous application of the methods of this invention is to provide an indicator of a relapsed cancer following therapy, or impending relapse, or treatment failure.

Another advantageous application of the methods of this invention is to identify humans or animals who might benefit from additional diagnostic procedures, wherein said procedures include but are not limited to surgery, biopsy, needle aspiration, radiologic imaging including X-ray, MRI, and CT scanning, radionucleotide imaging, colonoscopy, sigmoidoscopy, bronchoscopy, endoscopy, PET scanning, stool analysis, sputum analysis, cystoscopy, pelvic examination including PAP, and physical examination.

The invention further provides diagnostic and research kits that enable quantitative, qualitative or other comparative assessment of total RNA or of specific RNA species in plasma, serum, or other bodily fluids. In one aspect, a kit according to this aspect of the invention can provide a reference range for normal values or values that are disease-related under conditions that enable identification or selection of a human or animal with a disease, most particularly cancer or neoplastic disease. In another aspect kits of this invention provide reagents for extracting total extracellular RNA from the bodily fluid, and/or reagents and/or probes and primers for the amplification of said RNA, and/or reagents and materials for the detection of RNA product, and/or reagents for hybridization of RNA, and/or standards and controls for the analysis of the test, or reagents or devices or tubes for collecting, handling, or storage of the bodily fluid, or any combination or variation thereof, wherein further the reagents may be standardized to be comparable with reagents used to define RNA values for the reference population.

The methods of the invention and preferred uses for the methods of the invention are more fully illustrated in the following prophetic Examples. These Examples illustrate certain aspects of the above-described method and advantageous results. These Examples are shown by way of illustration and not by way of limitation.

EXAMPLE 1

Comparative Analysis of Two Extracellular RNA Species, and Application of a Stabilizing Agent:

Comparative analysis for two tumor-related mRNA, Her-2/neu RNA and hTERT RNA, in plasma will be evaluated in quantitative fashion in a human. Blood is to be drawn in a local laboratory facility using an EDTA containing vacutainer tube. Within 3 hours following venipuncture, the blood specimen is to be centrifuged at 3000×g for 15 minutes, and then Trizol 2 milliliters is to be added to 2 milliliters of plasma. The plasma specimen mixed with Trizol is then shipped to a central laboratory. Total RNA is to be extracted from plasma according to manufacturer's instructions using Trizol. The extracted RNA from 50 microliters of plasma was then reverse transcribed and Her-2/neu cDNA and hTERT cDNA amplified quantitatively using Taqman and using cDNA-specific primers. The amount or concentration of each RNA species is to be comparatively analyzed, thereby supporting a diagnosis of breast cancer. The assay is to be repeated serially throughout treatment thereby enabling the characterization of the cancer and monitoring response to therapy.

EXAMPLE 2

Clinical Application:

A 52 year-old woman with no symptomatic evidence of disease will present for routine cancer screening. Her physician draws a plasma specimen for assay. Total extracellular RNA is extracted from the patient's plasma, and the extracted extracellular RNA amplified quantitatively using Taqman PCR technology for a housekeeping gene RNA or similar standard RNA such as c-abl RNA, and for a tumor-associated RNA such as EGFr RNA. In this case the woman's quantitative levels of EGFr RNA are substantially elevated in comparison to an EGFr RNA reference standard for healthy patients without cancer, while levels of c-abl RNA are consistent with the normal reference range of c-abl RNA in plasma from healthy patients without cancer. The difference between the two ratios indicates that either the presence of cancer, or a high risk of developing cancer, is therefore identified for the woman.

EXAMPLE 3

Detection of a Translocated Gene RNA:

A 48 year-old man with acute promyelocytic leukemia will be monitored during therapy using the methods of the invention. The patient's blood plasma sample will be obtained, total RNA extracted from the plasma, reverse transcription performed upon the extracted RNA to produce cDNA and a portion of the cDNA quantitatively amplified by RT-PCR for a cDNA corresponding to PML/RAR RNA, a translocated gene RNA that characterizes acute promyelocytic leukemia. Quantitative levels of plasma PML/RAR RNA will be determined in a serial manner over a period of time while the patient is receiving therapy, thereby enabling monitoring of treatment. A reduction in plasma PML/RAR RNA levels from baseline will indicate a response to treatment.

EXAMPLE 4

Cancer Screening by Detection of a Fusion Gene RNA:

A 72 year-old asymptomatic man will be screened for prostate cancer using the inventive methods. Blood plasma will be obtained from the man, total RNA extracted from the plasma, and a portion of the extracted RNA amplified for TMPRSS2/ERG RNA, a fusion gene RNA that characterizes some prostate cancers. In this case, TMPRSS2/ERG RNA will be detected in the plasma indicating a higher risk for prostate cancer in the man. Consequently, the man will subsequently undergo an ultrasound and needle biopsy of his prostate, and a histological diagnosis of prostate cancer will be confirmed.

It should be understood that the foregoing disclosure emphasizes certain specific embodiments of the invention and that all modifications or alternatives equivalent thereto are within the spirit and scope of the invention as set forth in the appended claims.

What is claimed is:

1. A method of detecting mRNA of a fusion gene in blood plasma or serum of a human, wherein said fusion gene is generated by chromosomal translocation, the method comprising the steps of:
    a) extracting RNA from blood plasma or serum of a human and producing extracted RNA;
    b) amplifying or signal amplifying a portion of the extracted RNA or cDNA derived therefrom, wherein the amplification is performed in either a qualitative or quantitative fashion using primers or labeled probes specific for the mRNA of said fusion gene or cDNA derived therefrom; and
    c) detecting an amplified product amplified from the mRNA of said fusion gene or cDNA derived therefrom, wherein the detection of said amplified product indicates that the mRNA of said fusion gene is present in the blood plasma or serum of the human.

2. The method of claim 1, wherein the amplification in step (b) is perfoitned by a method that is reverse transcriptase polymerase chain reaction, ligase chain reaction, branched DNA signal amplification, a method using amplifiable RNA reporters, Q-beta replication, transcription-based amplification, isothermal nucleic acid sequence based amplification, self-sustained sequence replication assay, boomerang DNA amplification, a method using strand displacement activation, or cycling probe technology.

3. The method of claim 1, wherein the detection of the amplified product in step (c) is performed using a detection method that is gel electrophoresis, capillary electrophoresis, detection using biotinylated or other modified primers, labeled fluorescent or chromagenic probes, laser-induced fluorescence, Southern blot analysis, Northern blot analysis, electroluminescence, reverse blot detection, mass spectroscopy, ELISA or high-performance liquid chromatography.

4. A method of detecting mRNA of a fusion gene in a non-cellular fraction of blood of a human, wherein said fusion gene is generated by chromosomal translocation, the method comprising the steps of:
    a) extracting RNA from a non-cellular fraction of blood of a human and producing extracted RNA;
    b) amplifying or signal amplifying a portion of the extracted RNA or cDNA derived therefrom, wherein the amplification is performed in either a qualitative or quantitative fashion using primers or labeled probes specific for the mRNA of said fusion gene or cDNA derived therefrom; and
    c) detecting an amplified product amplified from the mRNA of said fusion gene or cDNA derived therefrom, wherein the detection of said amplified product indicates that the mRNA of said fusion gene is present in the non-cellular fraction of blood of the human.

5. The method of claim 4, wherein the amplification in step (b) is performed by a method that is reverse transcriptase polymerase chain reaction, ligase chain reaction, branched DNA signal amplification, a method using amplifiable RNA reporters, Q-beta replication, transcription-based amplification, isothermal nucleic acid sequence based amplification, self-sustained sequence replication assay, boomerang DNA amplification, a method using strand displacement activation, or cycling probe technology.

6. The method of claim 4, wherein the detection of the amplified product in step (c) is performed using a detection method that is gel electrophoresis, capillary electrophoresis, detection using biotinylated or other modified primers, labeled fluorescent or chromagenic probes, laser-induced fluorescence, Southern blot analysis, Northern blot analysis, electroluminescence, reverse blot detection, mass spectroscopy, ELISA or high-performance liquid chromatography.

7. A method of producing cDNAs comprising cDNA of a fusion gene from RNA extracted from a non-cellular fraction of blood of a human, wherein the fusion gene is generated by chromosomal translocation, the method comprising the steps of reverse transcribing extracellular RNA present in RNA extracted from a non-cellular fraction of blood from a human using a reverse transcriptase and producing the cDNAs comprising said cDNA of said fusion gene using oligodeoxynucleotide primers when the mRNA of said fusion gene is present in said extracellular RNA.

8. A method of detecting two tumor-associated RNA species in blood plasma or serum of a human, wherein one of the two tumor-associated RNA species is mRNA of a fusion gene generated by chromosomal translocation, the method comprising the steps of:
- a) extracting RNA from blood plasma or serum of a human and producing extracted RNA;
- b) amplifying or signal amplifying in a sequential or concurrent manner a portion of the extracted RNA or cDNA derived therefrom, wherein amplification is performed in either a qualitative or quantitative fashion using primers or labeled probes specific for each of the two tumor-associated RNA species or cDNAs derived therefrom; and
- c) detecting two different amplified products amplified from each of the two tumor-associated RNA species or cDNAs derived therefrom, wherein the detection of said two different amplified products indicates that said two tumor-associated RNA species are present in the plasma or serum of the human.

* * * * *